US008424367B2

(12) United States Patent
Ploehn et al.

(10) Patent No.: US 8,424,367 B2
(45) Date of Patent: Apr. 23, 2013

(54) SYSTEMS AND METHODS FOR MEASUREMENT OF GAS PERMEATION THROUGH POLYMER FILMS

(75) Inventors: Harry J. Ploehn, Columbia, SC (US); John R. Monnier, Columbia, SC (US); Xiaoming Chen, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 261 days.

(21) Appl. No.: 12/397,520

(22) Filed: Mar. 4, 2009

(65) Prior Publication Data

US 2010/0223979 A1    Sep. 9, 2010

(51) Int. Cl.
*G01N 15/08* (2006.01)

(52) U.S. Cl.
USPC ............................................................. 73/38

(58) Field of Classification Search .................. 73/38
See application file for complete search history.

(56) References Cited

U.S. PATENT DOCUMENTS

| | | | |
|---|---|---|---|
| 3,223,597 A | 12/1965 | Hersch | |
| 3,590,634 A | 7/1971 | Pasternak et al. | |
| 3,926,561 A * | 12/1975 | Lucero | 436/178 |
| 4,468,951 A | 9/1984 | Garcia et al. | |
| 4,656,865 A | 4/1987 | Callan | |
| 4,815,316 A | 3/1989 | Tantram | |
| 4,973,395 A | 11/1990 | Mayer et al. | |
| 5,139,638 A | 8/1992 | Mayer | |
| 5,142,143 A * | 8/1992 | Fite et al. | 250/288 |
| 5,318,752 A * | 6/1994 | Visser | 422/83 |
| 5,403,464 A | 4/1995 | Mayer et al. | |
| 5,513,515 A | 5/1996 | Mayer | |
| 5,591,898 A | 1/1997 | Mayer | |
| 5,723,769 A | 3/1998 | Barber | |
| 5,817,924 A * | 10/1998 | Tuomela et al. | 73/38 |
| 6,335,202 B1 | 1/2002 | Lee et al. | |
| 6,422,063 B1 * | 7/2002 | Anantheswaran et al. | 73/38 |
| 6,766,682 B2 | 7/2004 | Engle et al. | |

(Continued)

OTHER PUBLICATIONS

Brubaker et al., "Apparatus for Measuring Gas Permeability of Sheet Materials", *Analytical Chemistry*, vol. 25, No. 3, 1953, pp. 424-426.

(Continued)

*Primary Examiner* — Hezron E Williams
*Assistant Examiner* — Mark A Shabman
(74) *Attorney, Agent, or Firm* — Dority & Manning, P.A.

(57) ABSTRACT

In accordance with one embodiment of the present disclosure, a system for determining the rate of gas permeation through a film is described. The system comprises a continuous flow permeation cell, a mass spectrometer, a test gas source, and a carrier gas source. The continuous flow permeation cell comprises a supply chamber in communication with the test gas source and a receiving chamber in communication with the carrier gas source and the mass spectrometer. The supply chamber is configured to be separated from the receiving chamber by a test film such that when a test gas stream is fed to the supply chamber from the test gas source and a carrier gas stream is fed to the receiving chamber from the carrier gas source. At least a portion of the test gas stream permeates from the supply chamber through the test film to the receiving chamber and mixes with the carrier gas stream and the mixture flows to the mass spectrometer. The mass spectrometer is utilized to determine the rate of permeation of the test gas stream through the film.

18 Claims, 9 Drawing Sheets

U.S. PATENT DOCUMENTS

| | | |
|---|---|---|
| 7,178,384 B2 | 2/2007 | Bujas et al. |
| 2002/0162384 A1* | 11/2002 | Sharp et al. ............ 73/38 |
| 2004/0134258 A1* | 7/2004 | Wang et al. ............ 73/38 |

OTHER PUBLICATIONS

Chern et al., "Selective Permeation of $CO^2$ and $CH^4$ Through Kapton Polyimide: Effects of Penetrant Competition and Gas Phase Nonideality", *Journal of Polymer Science: Polymer Physcis Edition*, vol. 22 (1984), pp. 1061-1084.

Daynes, "The Process of Diffusion Through a Rubber Membrane", *Proceedings of the Royal Society of London, Series A*, vol. 97, No. 685 (1920), pp. 286-307.

Johnson et al., "Membrane Introduction Mass Spectrometry Trends and Applications", *Mass Spectrometry Reviews*, vol. 19 (2000), pp. 1-37.

Jordan et al., "Permeability of Pure and Mixed Gases in Silicone Rubber at Elevated Pressures", *Journal of Polymer Science: Part B: Polymer Physics*, vol. 28 (1990), pp. 795-809.

O'Brien et al., "A New Technique for the Measurement of Multicomponent Gas Transport Through Polymeric Films", *Journal of Membrane Science*, vol. 29 (1986), pp. 229-238.

Papiernik et al., "An Apparatus for Measuring the Gas Permeability of Films", *Journal of Environmental Quality*, vol. 31 (2002), pp. 358-361.

Pasternak et al., "A Dynamic Approach to Diffusion and Permeation Measurements", *Journal of Polymer Science: Part A-2: Polymer Physics*, vol. 8 (1970), pp. 467-479.

Pye et al., "Measurement of Gas Permeability of Polymers. II. Apparatus for Determination of Permeabilities of Mixed Gases and Vapors", *Journal of Applied Polymer Science*, vol. 20 (1976), pp. 287-301.

Ranade et al., "High Sensitivity Gas Permeability Measurement System for Thin Plastic Films", *Review of Scientific Instruments*, vol. 76 (2005), p. 013902.

Rogers et al., "Diffusion Coefficient, Solubility and Permeability for Helium in Glass", *Journal of Applied Physics*, vol. 25, No. 7 (1954), pp. 868-875.

Rutherford et al., "Review of Time Lag Permeation Technique as a Method for Characterisation of Porous Media and Membranes", *Absorption*, vol. 3 (1997), pp. 283-312.

Schafer et al., "Coupled Pervaporation/Mass Spectrometry for Investigating Membrane Mass Transport Phenomena", *Journal of Membrane Society*, vol. 241 (2004), pp. 197-205.

Stern et al., "Performance of a Versatile Variable-Volume Permeability Cell. Comparison of Gas Permeability Measurements by the Variable-Volume and Variable-Pressure Methods", *Journal of Applied Polymer Science*, vol. 7 (1963), pp. 2035-2051.

Tremblay et al., "Gas Permeability, Diffusivity and Solubility of Nitrogen, Helium, Methane, Carbon Dioxide and Formaldehyde in Dense Polymeric Membranes Using a New On-line Permeation Apparatus", *Journal of Membrane Science*, vol. 282 (2006), pp. 245-256.

Watson et al., "Precise Static and Dynamic Permeation Measurements Using a Continuous-Flow Vacuum Cell", *Journal of Membrane Science*, vol. 106 (1995), pp. 259-268.

Yasuda, "Isobaric Measurement of Gas Permeability of Polymers", *Journal of Applied Polymer Science*, vol. 14 (1970), pp. 2839-2877.

Yeom et al., "Precise On-line Measurements of Permeation Transients Through Dense Polymeric Membranes Using a New Permeation Apparatus", *Journal of Membrane Science*, vol. 161 (1999), pp. 55-66.

Yeom et al., "Analysis of Permeation Transients of Pure Gases Through Dense Polymeric Membranes Measured by a New Permeation Apparatus", *Journal of Membrane Sicence*, vol. 166 (2000), pp. 71-83.

Yeom et al., "Vapor Permeations of a Series of VOCs/$N^2$ Mixtures", *Journal of Membrane Science*, vol. 198 (2002), pp. 129-143.

Ziegel et al., "Measurement of Hydrogen Isotope Transport in Poly-(vinyl fluoride) Films by the Permeation-Rate Method", *Journal of Polymer Science: Part A-2: Polymer Physics*, vol. 7 (1969), pp. 809-819.

* cited by examiner

TABLE I

TIME CONSTANTS MEASURED IN GAS BURST TESTS.

| FLOW RATE (cc/min) | $t_d - t_0$ (second) | $t_p - t_0$ (second) |
|---|---|---|
| 5.0 | 132,130,149 | 420,418,409 |
| 10.0 | 65,66,64 | 186,191,190 |
| 15.0 | 36,28,34 | 116,120,119 |

FIG. 12

DIFFUSIVITY VALUES

| TEST | $S_{CO2} \times 10^4$ (amp/torr) | $D_{CO2} \times 10^{10}$ (cm$^2$/sec) | $P_{CO2} \times 10^{14}$ (cm$^3$·sec)/(cm$^2$·s·Pa) |
|---|---|---|---|
| 1 | 1.27 | 5.06 | 1.12 |
| 2 | 1.27 | 5.09 | 1.16 |
| 3 | 0.553 | 5.38 | 1.15 |

TABLE II

FIG. 13

SYSTEMS AND METHODS FOR MEASUREMENT OF GAS PERMEATION THROUGH POLYMER FILMS

BACKGROUND

The gas permeability of polymer films is very important in a variety of packaging applications. For example, for many food and beverages, the package's resistance to oxygen and water intrusion is the limiting factor for their shelf lives. Today, new and more stringent packaging standards are being issued to address the public concerns on the health safety, energy, and environmental issues related to plastics packaging. This has triggered a new wave of development of novel gas barrier films, usually with aims for lower gas permeability. At the same time, the demand for fast, accurate, and versatile gas permeation test systems is also on the rise. However, it becomes increasingly difficult to quickly and accurately characterize the permeabilities of new film products as the permeabilities are being reduced to unprecedented low levels. Hence, there is also an acute need to advance the state of the art of gas permeability measurement in parallel with the material development.

Experimental methods for permeation rate measurement have undergone development for more than a century. The two general methods are the variable-pressure (manometric) method and the variable-volume (volumetric) method. Both have been standardized by American Society of Testing Methods (ASTM) since the 1950s such as in ASTM method D1434-82, which is incorporated by reference herein. In the manometric method, a gas permeates through a film into a closed constant-volume chamber that is pre-evacuated. The pressure rise in the chamber is recorded as a function of time by reading displacement of mercury in a capillary (manometer). In the volumetric method, the chamber into which a gas permeates is allowed to expand against a low constant pressure (usually atmospheric). The volume change of the chamber is recorded as a function of time by reading displacement of a liquid in a capillary. The two methods provide for the determination of steady-state gas permeation rate, permeance (i.e., the ratio of the gas permeation rate to the difference in partial pressure on the two sides of the film), and, in the case of homogenous materials, permeability. The repeatability and reproducibility of the two methods are satisfactory and the data agreement between the two methods is also good. For these reasons, the two methods have been widely used.

However, the manometric and the volumetric methods have two disadvantages. First, these methods record integrated information (pressure or volume), rather than differential rate information. An experimental curve recorded in this way has transient and steady state components. The transient part precedes the steady state and is shown as a nonlinear pressure rise with time. At the steady state, the change of pressure with time becomes linear. There is a time lag between the time when the penetrant enters the test film and the time when the permeation process reaches the steady state. The diffusion coefficient, solubility coefficient and permeability coefficient of the test film can be determined by correlating the observed time-lag with mathematical diffusion models. This technique is called the time-lag analysis, which is the only viable analysis for the determination of the transport coefficients for the two methods. Though in theory transient permeation rates can be obtained by differentiating a time-lag curve with respect to time, it is not recommended for practice because numerical differentiation is prone to error and the worst signal-to-noise ratio is always found in the primary region of interest (i.e., where the nonlinear rise developed just as the curve departs from the baseline prior to its linear growth). Consequently, the manometric and the volumetric methods give apparent properties rather than intrinsic ones. For example, if the diffusion coefficient of the test film is non-constant in the process, the use of the time-lag technique will lead to an apparent diffusion coefficient which may be significantly different from the intrinsic diffusion coefficient. Moreover, the permeation test has to be carried out to the steady state. The time required to reach steady state will depend on the nature of the specimen, its thickness, and the applied pressure differential. For specimens of low permeability, long periods of test and repeated measurement may be required to obtain reliable results. Second, as the methods of recording pressure change or volume change are indifferent to gas composition, individual gas permeation in a gas mixture cannot be differentiated by either of the methods. Hence, the manometric and the volumetric methods are ideal for studying pure gas permeation only. There can be a question as to whether the permeability determined for pure gases can be used for multi-component gas permeation processes. Therefore the application range of the manometric and volumetric methods is rather limited.

Clearly, there is a need to measure transient permeation rate so that intrinsic properties can be obtained and test period can be shortened. There is also a need to overcome the lack of selectivity in the manometric and the volumetric methods. The problems can be solved by choosing a suitable gas detecting method in place of the old pressure- or volume-recording method. In literature, usages of thermal conductivity detector, coulometric detector, infrared spectrometer, gas chromatograph (GC) and mass spectrometer (MS) have been reported for measurement of gas permeability of polymers. For example, various measurement methods are described based on the principle of the thermal conductivity of gas mixtures. Though gas transmission rate may be automatically recorded by these methods, the usage of thermal conductivity detector alone does not solve the selectivity problem. Coulometric detectors are used in commercial devices sold by Mocon Inc. for measuring oxygen and water vapor transmission rates, respectively. Infrared water vapor sensors are also used by the same company for measuring water vapor transmission rates. Again, these commercialized methods lack the selectivity in gas measurement as one type of sensor can only detect one specific type of gas. In terms of selectivity, however, GC and MS are probably the most promising techniques.

GC has been used for the analysis of multi-component gas permeation. In common the current methods use an ionic pressure gauge or a thermal conductivity detector to continuously monitor the change of the total gas pressure and use GC to analyze gas composition. The major difference lies in how the permeation cell is designed to interface with GC. There are two major types of permeation cells: continuous flow cell and vacuum cell. The continuous flow cell includes two compartments separated by a test film. The test gas is introduced into one compartment and interacts with the upstream face of the test film; a carrier (or sweep) gas flows at constant rate in the other compartment and interacts with the downstream face of the test film. The permeant that diffuses through the test film is swept by the carrier gas and transferred to the gas detector relatively far downstream. Compared with the vacuum cell, the continuous flow cell has some advantages: (1) little or no film support is required as pressures can be balanced between the two compartments; (2) leakage should have a minimum effect on the testing results; (3) the conditioning time may be shortened as there is no need for degassing. As carrier gases are used in the GC technique, it is relatively easy to place a GC at the downstream of a continuous flow cell and use the same carrier gas for both the permeation cell and the GC. However, accurate control of the carrier gas flow rate is important, and undesirable back diffusion of carrier gas can occur to a measurable extent. To avoid using a downstream sweep gas, some methods use a vacuum cell design, with the downstream compartment pre-evacuated. Since such a vacuum cell is a variant of the manometric vacuum cell, it has the same disadvantages, such as film distention/rupture, leak, or the like. The common problem with these GC methods is that the gas composition analysis is operated in a batch mode rather than a continuous mode as the rate of composition analysis is restricted by the response time of a GC and the length of time required to complete a gas chromatographic analysis of a potentially complex gas mixture (typically 5-20 minutes). Therefore, it is doubtful that the GC methods can effectively measure transient permeation rates particularly when the rates are high. Moreover, the GC streams must be accurately controlled and carefully calibrated for each separation scheme and each operating condition.

Mass spectrometers used for gas analysis are commonly referred to as residual gas analyzers. It is desirable to have a single source detector that can measure partial pressures quickly. A residual gas analyzer (referred to herein interchangeably as "residual gas analyzer", "mass spectrometer", or "MS") offers this advantage for a wide range of gases. It allows the partial pressures of gas components to be determined simultaneously, an operation which is not possible with either a GC or an absolute pressure gauge. Because a MS must operate at high vacuum conditions, traditionally the modified vacuum cell was used to couple with MS. Designs have been described for pervaporation. In such designs, an absolute pressure gauge was used to monitor the vapor pressure in the pre-evacuated downstream compartment. A small aperture of known area was placed between the compartment and an MS, which restricts the molecular flow rate and reduces the leak rate to a negligible level compared to the pressure before the aperture. The permeation transient was calculated from an empirical formula once the pressure before the aperture, the aperture area and gas property are known. However, suppose the pressure after the aperture is $10^{-6}$ torr, the pressure before the aperture must be $10^{-3}$ torr or greater in an ante chamber to apply the formula. If the volume of this ante chamber is too large, the residence time of permeants in this ante chamber at $10^{-3}$ torr can be so long that transient rates are not attainable; this is known as a memory effect, and refers to the length of time between permeation and detection. This implies that the estimation of the permeation transient in the initial stage is not likely accurate. Nevertheless, it has been concluded that the total pressures as measured by the MS and by the pressure gauge agree well enough and hence the measurement of permeation transient should be possible. Similar designs have been used for the pervaporation process. Note that with such designs, the pressure before the aperture is accumulated during the measurement, meanwhile the pressure after the aperture changes accordingly. Therefore, error will be introduced into the calculation of the molecular flow rate at the end of the process. Moreover, a potential risk with the vacuum cell design is that the MS may be over-pressured, either because of the accumulation of pressure or because of an accidental film rupture event. Protection must be taken, usually with the aid of a bypass valve set at a safe pressure. Consequently, it is not always possible for a permeation experiment to reach steady state. Recently, designs have been described in which the absolute pressure measurement and the MS detection occurred in the same high vacuum chamber. Such designs have a higher risk of over-pressuring the MS. As a result, impractically low pressures ($10^{-5}$ to 0.13 atm) have been applied on the upstream side of the specimen film in such designs.

In contrast to a vacuum cell, the pressure in a continuous flow cell can be maintained at a steady value, as can the pressure before the MS. This avoids the complications in a vacuum cell as discussed above. The major concern with the continuous flow cell is the dilution effect by the sweep gas, which may lower the permeant concentration to an undetectable level. So far, coupling of MS and the continuous flow cell has rarely been seen.

Thus, a need exists for improved methods for measuring permeation rates. In particular, any method that can measure permeation rates of either pure or mixture gases would also be desirable. Systems for carrying out such methods would be particularly beneficial.

SUMMARY

In accordance with one embodiment of the present disclosure, a system for determining the rate of gas permeation through a film is described. The system comprises a continuous flow permeation cell, a mass spectrometer, a test gas source, and a carrier gas source. The continuous flow permeation cell comprises a supply chamber in communication with the test gas source and a receiving chamber in communication with the carrier gas source and the mass spectrometer. The supply chamber is configured to be separated from the receiving chamber by a test film such that when a test gas stream is fed to the supply chamber from the test gas source and a carrier gas stream is fed to the receiving chamber from the carrier gas source. At least a portion of the test gas stream permeates from the supply chamber through the test film to the receiving chamber and mixes with the carrier gas stream and the mixture flows to the mass spectrometer. The mass spectrometer is utilized to determine the rate of permeation of the test gas stream through the film.

In certain embodiments, a method for determining the rate of gas permeation through a film is described. The method includes feeding a test gas stream through a test film in a system, the system comprising a continuous flow permeation cell, a mass spectrometer, a test gas source, and a carrier gas source.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which:

FIG. 12 (also referred to as TABLE I) illustrates time constants measured in gas pulse tests in accordance with certain embodiments of the present disclosure;

FIG. 13 (also referred to as TABLE II) illustrates diffusivity values in accordance with certain embodiments of the present disclosure.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally directed to systems and methods for measurement of permeation rates. The current designs are motivated by the need to measure the transient permeation rates of either pure or mixture gases in a direct, rapid, precise and selective manner. In accordance with the present disclosure, a MS is coupled to a continuous flow cell in order to avoid the drawbacks of vacuum permeation cells. The systems and methods of the present disclosure allow for $CO_2$ permeability test results that are comparable to that obtained with a Mocon instrument.

Figure 1:
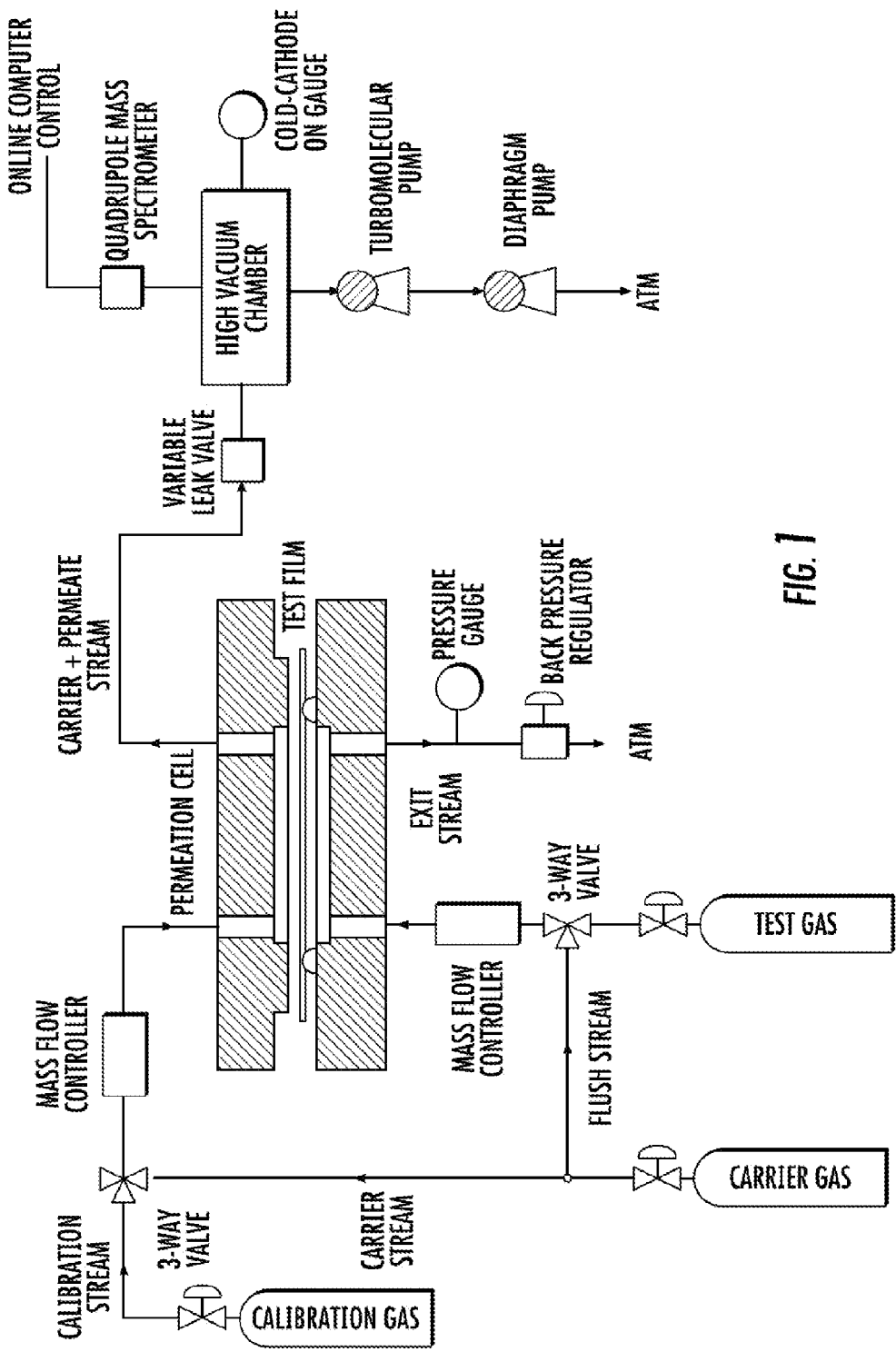
FIG. 1 illustrates a schematic diagram of a gas permeation apparatus in accordance with certain embodiments of the present disclosure.

A system that accomplishes the objectives set forth in the introduction is schematically illustrated in FIG. 1. The gas permeation apparatus includes at least the following components: (1) a continuous-flow permeation cell, (2) a quadrupole mass spectrometer, (3) an ultra-high vacuum chamber, (4) a vacuum pumping system, (5) a gas sampling system, (6) gas supplies and flow controls and (7) software and hardware for online measurement. Each component is explained in detail herein.

Under normal operational conditions, a test gas is passed through one side of the permeation cell and at the same time an inert carrier gas stream is passed through the other side of the permeation cell. The exit stream on the test gas side is passed through a variable back pressure regulator before it is discarded into the atmosphere. The exit stream on the carrier gas side contains the gas permeate and its pressure is normally at one atmosphere. A large portion of this exit stream is also discarded, while a small amount of it is leaked into a high vacuum chamber to be analyzed by a quadrupole mass spectrometer. The ion current signals produced by the quadrupole mass spectrometer are collected online by the computer software and hardware controls. The pressure of the high vacuum chamber is monitored by the MS and also independently by a cold-cathode ion gauge. The gas permeation tests are routinely performed at room temperature (about 23° C.) and with nearly zero absolute pressure difference across the film. Nevertheless, it is not difficult to add a temperature control (encompassing the permeation cell and related tubing) to allow measurement at higher temperatures, and a pressure differential can be applied by adjusting the back pressure regulator.

Figure 2:
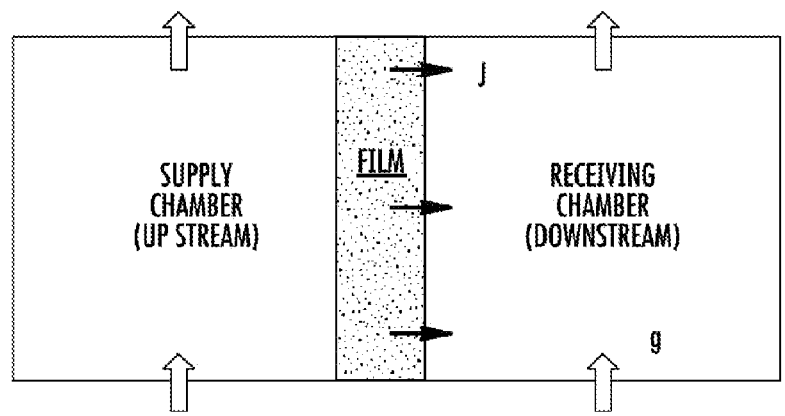
FIG. 2 illustrates a continuous-flow permeation cell in accordance with certain embodiments of the present disclosure.

Conceptually, a continuous-flow permeation cell consists of two chambers separated by a testing film, as shown in FIG. 2. Both chambers are constant in volume and allow flowing gas streams. The chamber into which a testing gas is introduced is called the supply chamber. The chamber into which an inert carrier (or sweeping) gas is introduced is called the receiving chamber. In the permeation process, the testing gas adsorbs and/or absorbs on the upstream side of the film and then diffuses through the film into the receiving chamber. The carrier gas continuously sweeps the downstream side of the film, and the effluent (including carrier gas and permeate) of the receiving chamber is transported to the MS gas detector for further analyses.

The use of a continuous-flow permeation cell is based on the assumption that the permeate is well mixed with the carrier gas at any instant. The carrier gas flow rate is constant, so the transient permeation rate of the target species equals the product of its concentration and the carrier gas flow rate. The rate of the concentration rise within the receiving chamber, as a function of the permeation flux J and the carrier gas flow rate q, is given by the differential mass balance equation:

$$V \frac{dC}{dt} = J \cdot A_m - q \cdot C \qquad (1)$$

Integration of Eq.(1) shows that the concentration will arise in the usual exponential manner, according to the expression:

$$C(t) = \frac{J(t) \cdot A_m}{q}(1 - e^{-\frac{q}{V}t}) \qquad (2)$$

where $A_m$ is the film area and V is the volume of the receiving chamber. The response time of the cell to J is therefore characterized by the time constant q/V. This time constant is relevant to any transient permeation flux. It can be seen that the smaller the volume of the receiving chamber or the larger the carrier gas flow rate, the faster the response time will be. The actual cell time constant is best determined by experiment. It is necessary to point out that the volume is not critical if the sole purpose of measurement is to obtain steady-state permeability.

Figure 3:
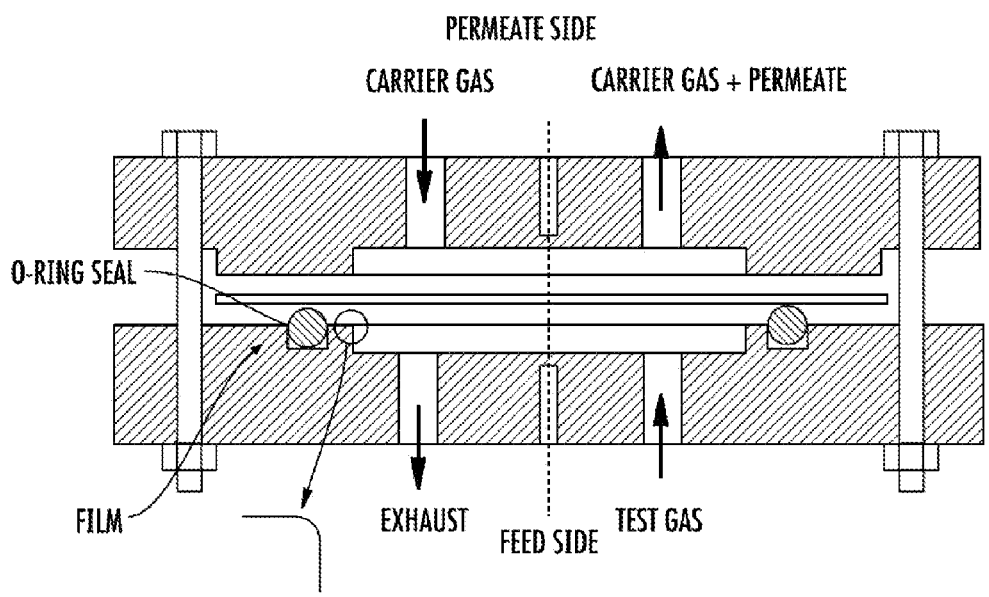
FIG. 3 illustrates a cross-sectional view of a permeation cell in accordance with certain embodiments of the present disclosure.

The actual permeation cell is comprised of two metal halves made of 316 stainless steel, as illustrated in FIG. 3. A thin circular cavity, which is 2" in diameter and 1/16" deep, is cut on each half cell. The edges of the cavities are rounded to avoid perforation of the specimen film. The two half cells are clamped by bolts and nuts and sealed by O-ring. The O-ring is placed in the groove machined on the half cell of the supply side. The half cell of the receiving side has an elevated rim with coated with surface polish, which defines the sealing area. In practice, a thin, continuous film of vacuum grease is also applied on the outer perimeter of the elevated rim to help the sealing. Each half cell also has a 1/8" diameter hole bored deep into the cell for mounting a thermocouple to accurately the temperature of the diffusion process. No structural support for the film is typically used as the gas permeation test is routinely performed with zero pressure difference across the film.

Quadrupole mass spectrometers (QMS) are well known for their low cost, fast response, and high sensitivity in residual gas analysis. In accordance with the present disclosure, the quadrupole mass spectrometer (QMS) is comprised of a quadrupole ionizer, a radio-frequency mass filter, a Faraday cup ion detector and an optional Channeltron electron multiplier. During the operation, the gas molecules are first positively charged by the ionizer, and then separated by the mass filter according to their mass-to-charge ratios. The positively charged gas molecules are neutralized on the surface of the Faraday cup or electron multiplier, which generates ion currents. The electron multiplier can further magnify the ion current signals by the mechanism of generating secondary electrons. The use of QMS as partial pressure analyzer is based on an ideal gas law (Dalton's law). It should be operated in vacuum (typically $<10^{-4}$ Pa or $<10^{-6}$ torr) so that the gas molecules do not interact with each other. An important index of a QMS is its dynamic response range, typically between $10^{-8}$ torr and $10^{-4}$ torr total pressure. The dynamic response range of the QMS determines the operation range of the permeation apparatus. When coupling a QMS with a continuous-flow permeation cell, the operation range is narrowed as the permeant is diluted by the carrier gas. Using an electron multiplier can broaden the operation range by improving the signal-to-noise ratio and thus lowering the lowest detection limit. For quantitative partial pressure analysis, it is necessary to calibrate the QMS for each and every permeating gas used.

A suitable quadrupole mass spectrometer for use with the present disclosure is the RGA-100 sold by Standford Research Systems of Sunnyvale, Calif. It is of low-resolution type with a scan range of 1-100 amu, sufficient for most industrial gases of interest. However, it should be understood that any suitable quadrupole mass spectrometer is contemplated for use with the present disclosure.

The vacuum pumping system includes a turbomolecular drag pump, a diaphragm pump, and accessories including an electronic control, cooling and power units. The turbomolecular drag pump overcomes the problem of backstreaming oil vapor contamination that exists in conventional oil diffusion vacuum pumps. It has a nominal pumping speed of 60 liters per second for nitrogen. The diaphragm pump serves as a backing pump that generates the necessary exhaust vacuum for the turbo pump and pumps the exhaust from the turbo pump against atmospheric pressure. It generates a rough vacuum around 1 mbar. The combination of the two pumps generates a high vacuum as low as 5e-9 mbar. Suitable pumps in accordance with the present disclosure include pumps sold by Pfeiffer Pumps, Inc. of Nashua, New Hampshire and include PFEIFFER TMU071P and PFEIFFER MVP015-2 model pumps.

A high vacuum chamber provides the necessary vacuum environment for the residual gas analysis in accordance with the present disclosure. A welded stainless steel union cross fitting can be selected for this purpose. In FIG. 1, the four openings of the cross are in turn jointed with the ionic gauge (right), the mass spectrometer (top), the gas sampling valve (left) and the vacuum pumps (bottom), using stainless fasteners, CF flanges and copper gaskets. However, any suitable vacuum-tight method of joining the components can be utilized. The vacuum pressure is referenced by a wide-range (5e-9 mbar to 1000 mbar) cold-cathode ion gauge such as a PFEIFFER PKR251. The ion gauge is used in the calibration of the QMS head pressure and the sensitivity factors. Suitable vacuum chambers include those sold by Swagelok Company of Solon, Ohio including the Swagelok JCF4C275 cross fitting.

The gas sampling system can include a variable leak valve, a 1/16" stainless tubing and a tee. The variable leak valve controls the rate of gas leak into the ultra-high vacuum chamber. It offers very high control sensitivity and stability with leak rates as small as $1 \times 10^{-10}$ torr·liters per second. The leak rate adjustment can be controlled with finger knobs. The vacuum pressure change as a result of leak rate adjustment can be read from the ionic gauge. The major advantage of using a variable leak valve is that it offers a wider operational vacuum range compared to the pressure-reduction methods that use fixed leak rate.

In accordance with certain embodiments of the present disclosure, a proper gas sampling design should ensure that the time response is fast and that the gas sampled is representative of the entire gas stream. The time response depends on the vacuum pumping rate and the dead volume of gas before the vacuum. If the gas being sampled has a dead volume of V and the gas pressure is p, the time needed to pass this gas pocket through vacuum is the product of p and V divided by the pumping rate. If the vacuum pressure is 1e$^{-6}$ torr and the pumping speed is 60 liters/second, then the pumping rate is 6e$^{-5}$ torr·liters/second. If the dead volume is 1 milliliter and the gas pressure is 760 torr (1 atm), it will take about 3.5 hours to replace the gas in the dead volume, which is not acceptable.

Figure 4:
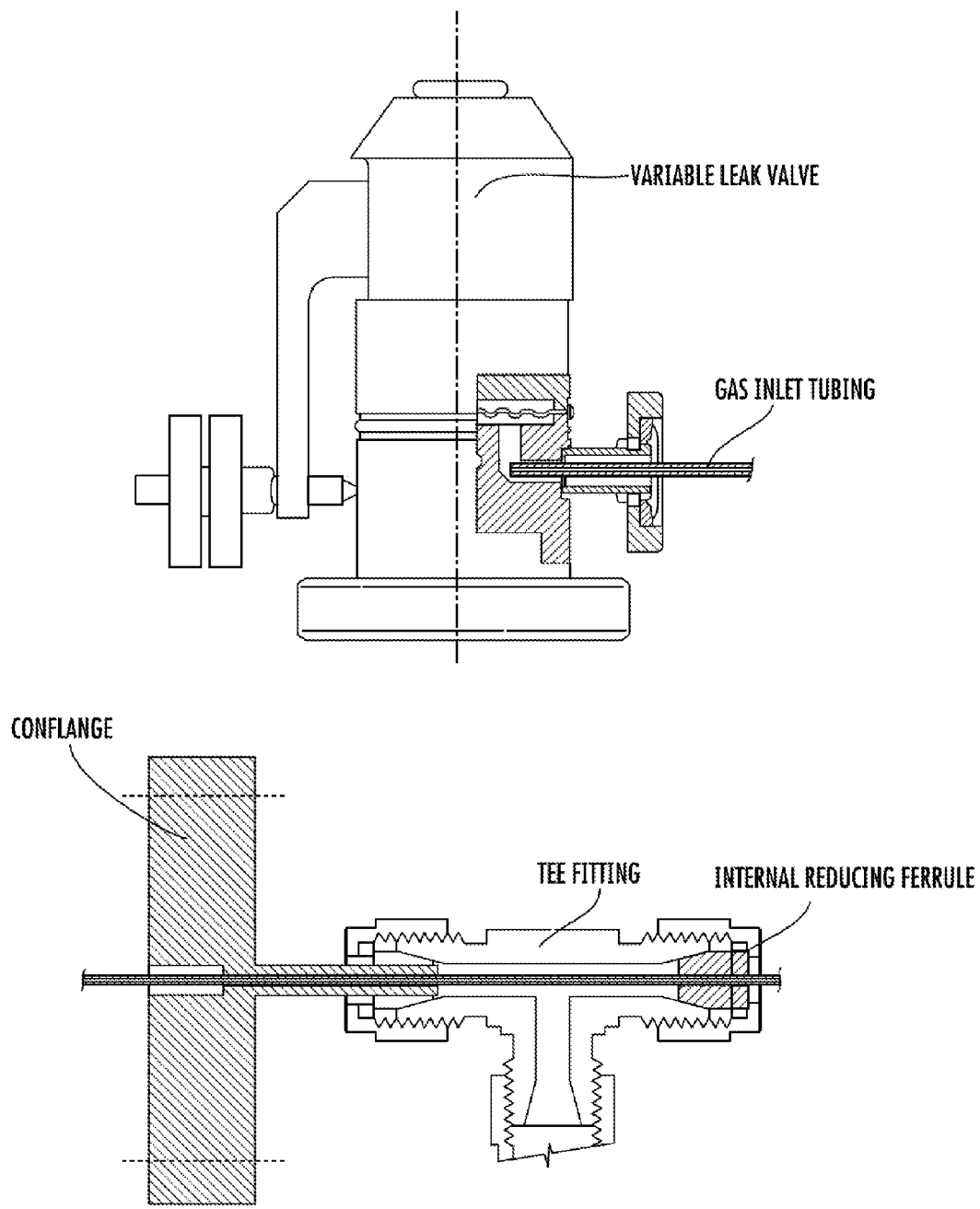
FIG. 4 illustrates the gas inlet connection for gas sampling in accordance with certain embodiments of the present disclosure.

Turning to FIG. 4, in certain embodiments of the present disclosure, the testing gas is fed through a 1/16" tubing, and the tubing is inserted to the end of the gas inlet channel of the variable leak valve in order to reduce the dead volume as much as possible. The gas inlet pressure for the variable leak valve is a little above 1 atm. The gap through which the gas enters the vacuum is very small. Normally only a small amount of gas will be sampled, and the rest will return in the same way as it enters and exhaust to the atmosphere. In general, a tubing of small inner-diameter is preferred as the smaller the cross section the higher the superficial gas velocity when the flow rate is constant. Beside the time delay due to dead volume, there is another time constant related to the mixing inside a confined volume. A similar analysis can be applied to compensate, just as described for the permeation cell. The actual time delay can be determined by experiment.

The gas supplies can include two compressed gas cylinders, one for testing gas, the other for carrier gas. Double-stage gas regulators can be used to reduce the outlet pressure of the compressed cylinder from about 2,500 to about 4,000 psi to lower than about 500 psi. The test gas can be either pure gas or mixture gas of known composition. The carrier gas should be of ultra-high purity and its flow rate should be precisely controlled.

Referring again to FIG. 1, three gas streams can be utilized. The first is the test gas flowing past the upstream side of the test film. The second is the carrier gas flowing past the downstream side of the test film. The third is the flush gas which is the same as the carrier gas and is used on the upstream side of the film to condition it before the analysis. All of the gas streams into the permeation cell are regulated by mass flow controllers. The test gas flow rate is usually not critical for permeability measurement provided that it is sufficiently high to maintain constant gas composition on the supply side of the film. However, it is desirable to have a mechanism to measure the delay time before the test gas reaches the permeation cell and to stabilize the double-stage gas regulator as it is more sensitive to the flow rate change than the pressure change in the compressed cylinder. The exit stream on the supply side is passed through a needle valve which provides a mechanism to control the back pressure.

The QMS is equipped with a RS232 communication port for transferring data to a computer equipped with either serial or USB port. However, any suitable communication method is contemplated for use with the present disclosure. In certain embodiments of the present disclosure, the online data acquisition can be managed by a Windows residual gas analysis software (RGA3_0) provided by Stanford Research Systems. However, any suitable software can be utilized in connection with the present disclosure.

It is assumed that the test gas that permeates through the test film is fully mixed in the carrier gas stream and its amount is negligibly small. Both assumptions can be easily satisfied in practice. The gas permeation rate $J_L(t)$ as evaluated at the downstream side of the test film is:

$$J_L(t) = C_L(t) \cdot q/A \tag{3}$$

where $C_L(t)$ is the concentration of the permeate at the downstream side of the film, q is the carrier gas flow rate and A is the permeation area of the test film. In certain embodiments of the present disclosure, q is set by the mass flow controller and A is also known; the only unknown is the permeate concentration, which has to be determined using the QMS. For this purpose, a small amount of the effluent carrier gas stream containing the permeate is leaked through the variable leak valve into the high vacuum chamber to be analyzed by the QMS. It is assumed that the sampled gas mixture is representative of the effluent gas stream. By assuring that the sampled gas mixture dominates the residual atmosphere in the vacuum chamber, the permeate concentration in the vacuum chamber is essentially the same as that in the effluent carrier gas stream. If the total pressure of the residual gases in the vacuum is $1 \times 10^{-8}$ torr, the test is preferably performed at $1 \times 10^{-6}$ torr or higher to give the highest practical signal intensity (ion current).

The QMS produces a mass spectrum in terms of ion currents, which consists of a series of ion peaks along the mass (mass-to-charge ratio) coordinate. The peak intensities can be quantitatively correlated with the partial pressures of the gas species. A single gas species can result in a mass spectrum with more than one ion peaks. Such a mass spectrum is called the fragmentation pattern and is unique to each gas species. In the case of a multicomponent gas mixture, the fragmentation patterns of the different gas components may overlap. The derivation of the partial pressures of a gas mixture is based on the assumption that the total spectrum is a linear combination of the spectra of the different species that are present in the mixture. The assumption is true when the gas mixture behaves like an ideal gas, or equivalently the vacuum chamber pressure is lower than $10^{-4}$ torr. In mathematical terms, the peak height at mass number M in a total spectrum, denoted as $I_M$, is written as:

$$I_M = \sum_g I_{Mg} \tag{4}$$

where g is an integer variable that represents a gas species in the mixture; M is an integer variable that represents a mass number for the entire mass range of the spectrum; $I_{Mg}$ is the contribution from gas g to the peak height at mass M. The partial pressure of gas g, $p_g$, is related to the fragmentation factor $\alpha_{Mg}$ and the QMS' sensitivity factor $S_g$ for gas g by the equation $$I_{Mg} = \alpha_{Mg} \cdot S_g \cdot p_g \tag{5}$$

Therefore, $$I_M = \sum_g \alpha_{Mg} \cdot S_g \cdot p_g \tag{6}$$

In Equation (6), $\alpha_{Mg}$ and $S_g$ are constants that can be measured. Thus, Equation (6) represents a linear system of equations with M equations and g unknown. Since all gases have more than one peak in their fragmentation patterns, the number of peaks (M) in a real spectrum is generally larger than the number of gases (g). Consequently, the system of equations usually has more equations than unknowns. The partial pressures can therefore be obtained by using all the equations and a multiple linear regression procedure to best-fit the data. Once the partial pressures are determined, the concentration of a gas component g is given by Dalton's law $$C_g = \frac{p_g}{\sum_g p_g} = \frac{p_g}{p_{total}} \tag{7}$$

where $p_{total}$ is the total vacuum chamber pressure. The permeation rate of gas g is obtained by substituting Equation (7) into Equation (3).

$\alpha_{Mg}$ and $S_g$ should be known in advance. Such variables are highly hardware-dependent and should be calibrated for each gas species involved in Equation (6). Quantitative partial pressure analysis by means of QMS to determine multiple $\alpha_{Mg}$ and $S_g$ can be somewhat time-consuming in order to carry out the above analysis. Nevertheless, in certain embodiments of the present disclosure, there are simpler situations in which the fragmentation patterns of the component gases in a mixture are found not to interfere with each other. For example, argon has a fragmentation pattern with peaks located at amu=20, 40 for the most plentiful $^{40}$Ar isotope (99.6% relative abundance), while carbon dioxide has a fragmentation pattern with peaks at amu=46, 45, 12, 16, 28, 44. If argon is chosen as the carrier gas in a $CO_2$ permeation test, monitor the principal peak at amu=44 for $CO_2$ and correlate $I_{44}$ with $p_{CO2}$. In this particular embodiment, $\alpha_{44,CO2}=1$, and Equation (6) can be reduced to the simplest form:

$$I_{44} = S_{CO_2} \cdot p_{CO_2} \tag{8}$$

The $CO_2$ permeation rate is therefore given by $$J_{CO_2}(t) = \frac{p_{CO_2}(t)}{p_{total}} \cdot \frac{q}{A} = \frac{q}{A} \frac{I_{44}(t)}{S_{CO_2} \cdot p_{total}} \quad (9)$$

Figure 5:
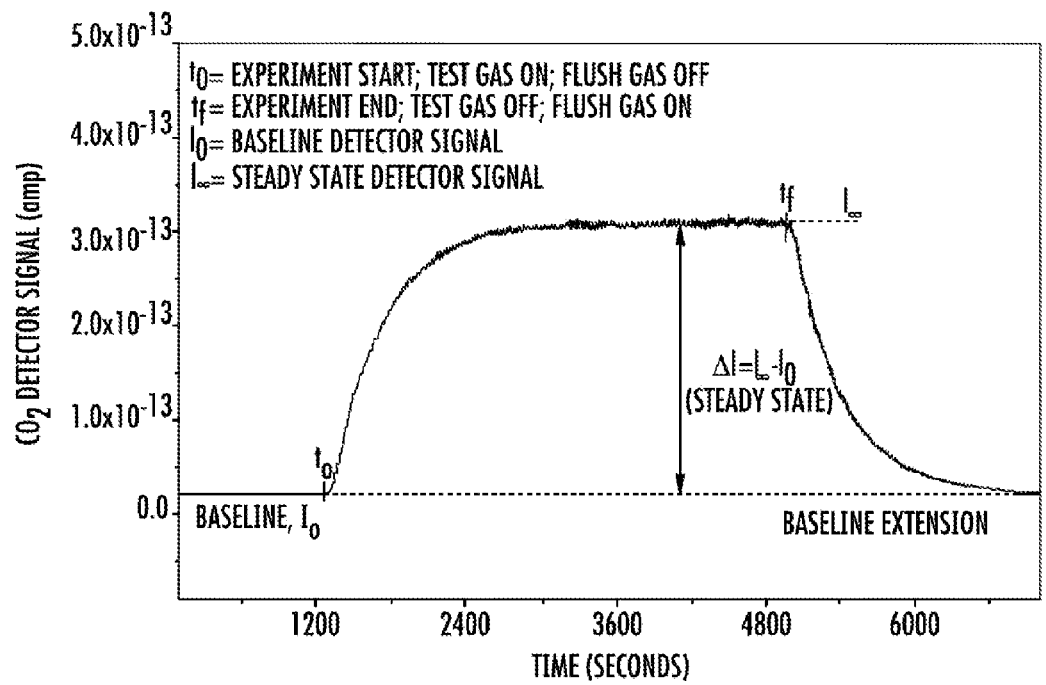
FIG. 5 illustrates a typical signal output monitored at amu=44 by the quadrupole mass spectrometer as function of time (the test film is a 3.6 micron thick Mylar® PET from Chemplex, the CEM was activated) in accordance with certain embodiments of the present disclosure.

To use Equation (9), it is assumed that the atmosphere in the vacuum chamber is dominated by the carrier gas and the permeate gas as illustrated in FIG. 5.

A typical signal output as function of time is given in FIG. 5, using the $CO_2$ permeation through a 3.6 micron thick Mylar® PET film as an example. The ion current signal was monitored at amu=44. Prior to testing, the test film was conditioned by flushing argon on both sides. The small, nonzero signals generated in this period established a baseline which is subtracted later. After the permeation test began, the signal ($I_{44}$) rose from the baseline after a lag time and reached a plateau at steady state. The continuous recording of the initial stage of permeation is more insightful than the manometric and the volumetric methods. The diffusion constant may be determined from the curve by the time lag analysis $$D = \frac{l^2}{6\theta} \quad (10)$$

where $l$ is the thickness of the test film and $\theta$ is the measured time lag. Or it may be determined by $$D = \frac{l^2}{7.2 \cdot t_{1/2}} \quad (12)$$

where $t_{1/2}$ is the half time for the permeation to reach steady state. The permeability constant may also be determined if the QMS ($S_{CO_2}$) is calibrated for $CO_2$. By definition, permeability P is the product of permeance and the thickness of a film, while permeance is the ratio of the gas permeation rate to the difference in partial pressure of the gas on the two sides of the film. Therefore, $$P_{CO_2} = \frac{q \cdot (I_\infty - I_0) \cdot l}{A \cdot S_{CO_2} \cdot p_{total} \cdot \Delta p} \quad (13)$$

The following Examples are intended to be purely exemplary of the present disclosure. In the Examples given below, experimental data are presented which show some of the results that have been obtained from embodiments of the present disclosure for different materials, temperatures, and processes.

EXAMPLE

Calibration

The partial pressure sensitivity factor of the QMS to a gas g, $S_g$, is defined as the ratio of the change in principal mass peak height to the corresponding change in total pressure due to a change in partial pressure of the particular gas species. The unit of $S_g$ is ion current per unit pressure, e.g., amp/mbar. The sensitivity value not only depends on the type of gas molecule but also on the operating parameters used for the device. For careful quantitative analysis, it is important that the sensitivity of the QMS be determined for every gas which may be a component of the system and at the same operating parameters used during the actual measurements. Sensitivity factors change over time due to aging and periodic recalibration is necessary. The gain of the electron multiplier is mass dependent and needs to be determined prior to performing measurements with the device. The gain characteristics of the electron multiplier also change with time and periodic recalibration is also necessary.

The basic procedure for determining the sensitivity for a particular gas is the following: (1) Introduce the pure gas into the vacuum system, at a known or calculable pressure, typically around $10^{-6}$ torr. (2) Measure the output signal from the QMS for the principal mass peak of that gas using the Faraday cup detector. (3) The ratio of this output signal to the pressure of the gas is the sensitivity factor, $S_g$. It is important to ensure that the partial pressures of all other gases in the system are small enough so that they may be neglected.

For the purpose of measuring transient gas permeation rates, it is also important for us to know if the sensitivity factors and the gains of the electron multiplier are constant during the measurement as the partial pressure of the permeate gas changes. Normally, a linear relation between the partial pressure and the corresponding QMS signals of gases is assured below $10^{-5}$ torr, and the linear gain of the electronic multiplier is also assured when the output current is lower than 10% of the bias current. For a typical resistance of 200M ohms, and a factory-set bias voltage of 1160 V, the bias current is 5.8 µamps. Since the gain at that voltage is roughly 1050 (determined for $N_2$), the maximum input current at which the output current behaves linearly is $-5 \times 10^{-9}$ amps. For a sensitivity of $10^{-4}$ amp/torr, this corresponds to an upper limit of $5 \times 10^{-5}$ torr. The gain of the electron multiplier changes with time. So the calculation only provides a guideline. The actual response of the QMS must be calibrated.

A fast calibration procedure has been developed which calibrated the MS for nitrogen and then obtained the partial pressure of other gases by multiplying with a correction factor found from literature. Although the concept is correct, the validity of the application is doubtful as the correction factors not just depend on the gas species and the pumping speed but also depend on the manufacture of instruments and their setups.

Figure 6:
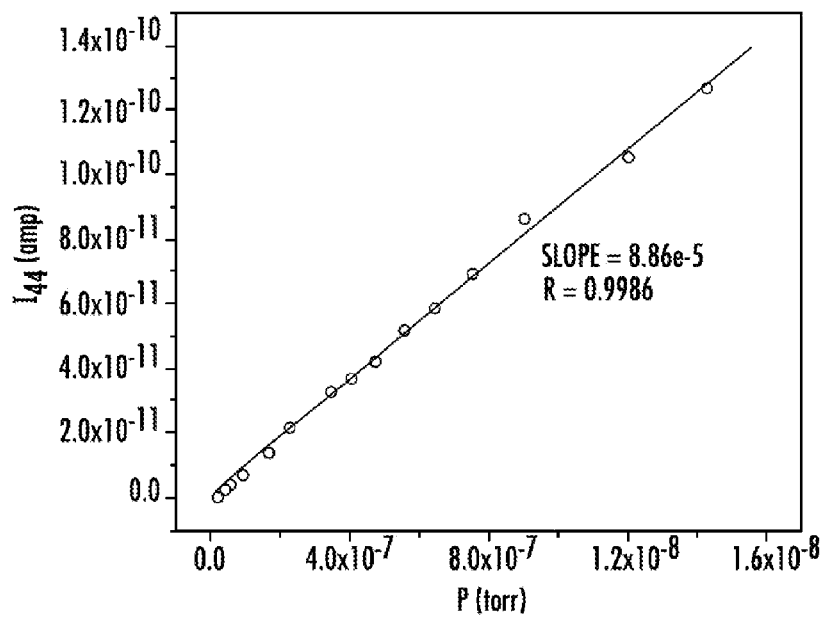
FIG. 6 illustrates variation of the ion currents at amu=44 with vacuum chamber pressure ($CO_2$-dominant environment) in accordance with certain embodiments of the present disclosure.

The results of two calibration experiments are presented to establish the linear working range of the QMS. In the first calibration, 99.5% pure $CO_2$ was leaked into the vacuum chamber at different desired vacuum pressures and the resulting ion currents at amu=44 were collected. The vacuum pressure was read from the cold-cathode ion gauge attached to the same vacuum chamber. The results are summarized in FIG. 6. In general, good linearity is found except at $<10^{-7}$ torr. The deviation from linearity in the high vacuum range is expected as the partial pressures of the other residual gases in the system become comparable to $CO_2$. The sensitivity factor for $CO_2$ was calculated as $0.886 \times 10^{-4}$ amp/torr by fitting a line to the data collected $>10^{-7}$ torr. Note that the default scaling factor used by the RGA_3.0 software is implicitly included in this sensitivity value.

The Faraday Cup (FC) detector is rarely used to measure partial pressures below $10^{-9}$ torr because the signal-to-noise ratio is very poor. This means that the FC detector is not usable if the vacuum pressure is around $10^{-6}$ torr and the permeate concentration is below 0.1%, a situation likely in an actual measurement. Raising the vacuum pressure has limited help as space-charge effects come into play at $>10^{-5}$ torr, which makes the sensitivity factor nonlinear. The electron multiplier should be used instead. The basic method of using pure gas to calibrate the sensitivity has two issues here. First, exposure to high partial pressures may easily saturate the electron multiplier and quickly degrade its performance. Second, the actual gain for the gas of interest with partial pressures below $10^{-9}$ torr cannot be accurately determined as the partial pressures of residual gases cannot be neglected when the vacuum chamber pressure is below $10^{-7}$ torr. For these reasons, it is recommended to calibrate the sensitivity factors along with the gain factors using a diluted gas mixture of known composition.

Figure 7:
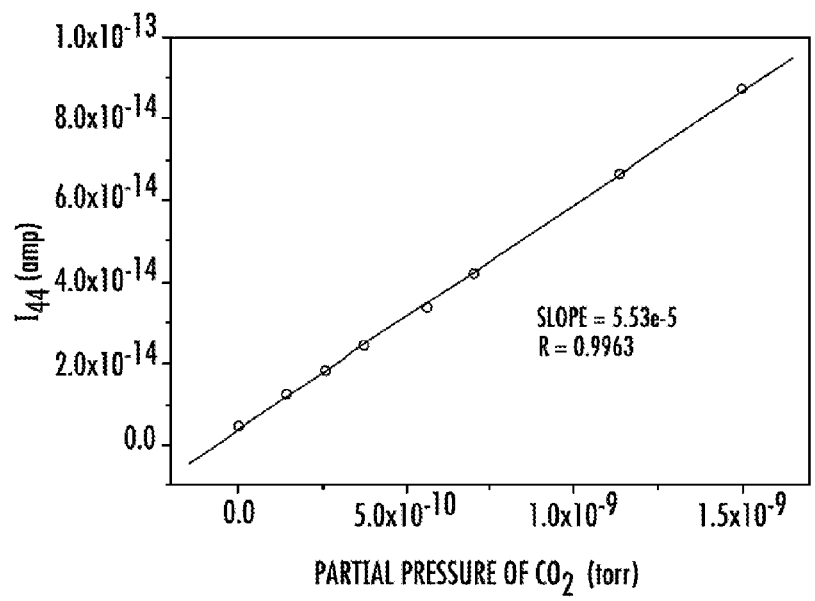
FIG. 7 illustrates variation of the ion current at amu=44 with $CO_2$ partial pressure when the vacuum chamber pressure is 0.75e-6 torr in accordance with certain embodiments of the present disclosure.

The result of the second calibration is presented here to establish the linearity of the response of the electronic multiplier to partial pressures. In the second calibration, a binary mixture of $CO_2$ and Ar was leaked into the vacuum chamber at a fixed vacuum pressure of $0.75 \times 10^{-6}$ torr. The $CO_2$ concentration in the binary mixture was varied from 0 to 2000 ppm. This was done by mixing two gas streams in a gas mixing manifold at varied flow rate ratios. One gas stream was 99.999% pure argon and the other was a NIST traceable binary mixture of 2000 ppm $CO_2$ in argon. The results are summarized in FIG. 7. In the studied $CO_2$ concentration range, good linearity is found. The sensitivity factor for $CO_2$ is obtained as 5.53e-5 amp/torr by fitting a line to the data. Note that the gain of electronic multiplier and the default scaling factor set by the RGA_3.0 software are implicitly included in this sensitivity value.

Adjustment of Gas Flow Rates

The test gas flow rate is not critical as long as a constant back pressure can be maintained on the upstream side of the test film. High flow rates should be used when high permeation rates are expected. There is a time delay for the test gas to travel from the gas switching valve to the permeation cell. If low flow rates are used, this time delay might be comparable to the intrinsic time lag of the test film. This time delay can be experimentally estimated (or measured) and subtracted from the apparent time lag. The flush gas flow rate is also not critical.

Figure 8:
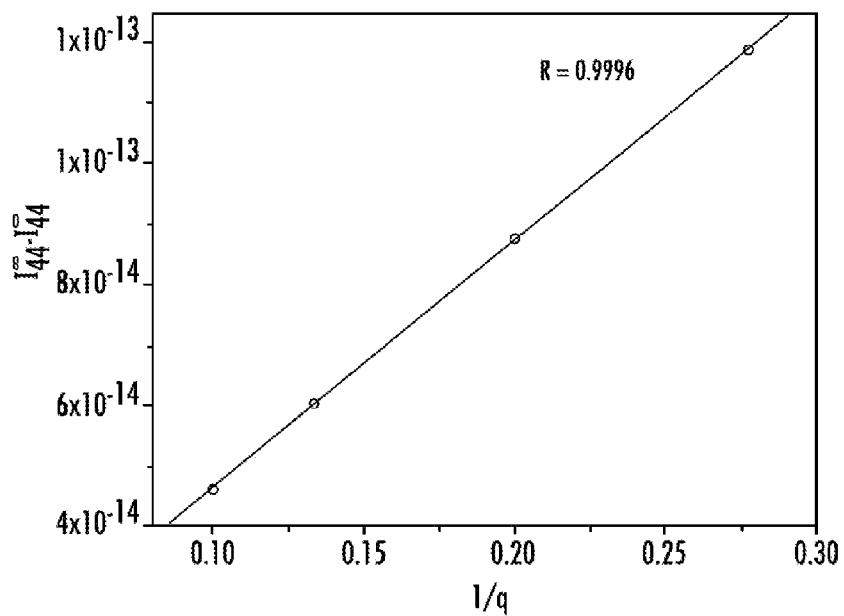
FIG. 8 illustrates variation of a steady-state detector signal with the reciprocal of carrier gas flow rate where the test gas is $CO_2$ in accordance with certain embodiments of the present disclosure.

The carrier gas flow rate must be precisely controlled as the calculation of permeability depends on this information. From Equation (3), the permeate concentration of the effluent stream to be analyzed is inversely proportional to the carrier gas flow rate. As the carrier gas flow rate decreases, the detector signal is increased. Hence when a low gas permeation rate is expected, using low carrier gas flow rate can help improve the signal quality. An example is shown in FIG. 8 to illustrate the effect of the carrier gas flow rate on the detector signal level. The data were collected by adjusting the carrier gas flow rate after the detector signal reached the steady state in a $CO_2$ permeation test. It can be seen that the relation between the signal and the reciprocal of q is linear, as Equation (3) indicates. The result also implies that the mixing is complete at these flow rates. In practice, carrier gas flow rate as low as about 2.0 cc/min may be used. However, it takes more time for the gas to travel from the permeation cell to the variable leak valve when the carrier gas flow rate is reduced. Low carrier gas flow rate is also expected to have a negative impact on the mixing in the variable leak valve, causing the dead time to increase.

Figure 9:
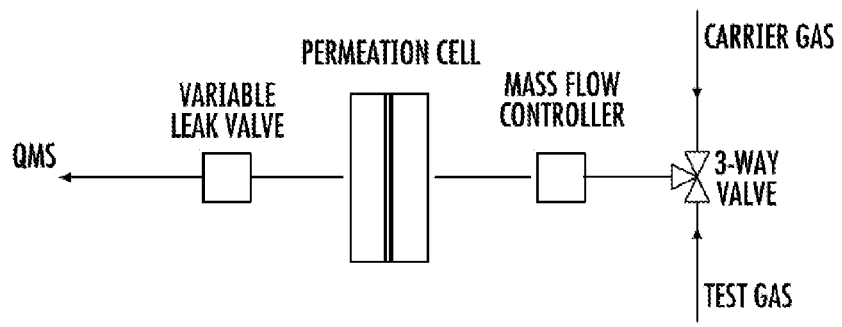
FIG. 9 illustrates a schematic drawing of the gas pulse experimental setup in accordance with certain embodiments of the present disclosure.
Figure 10A:
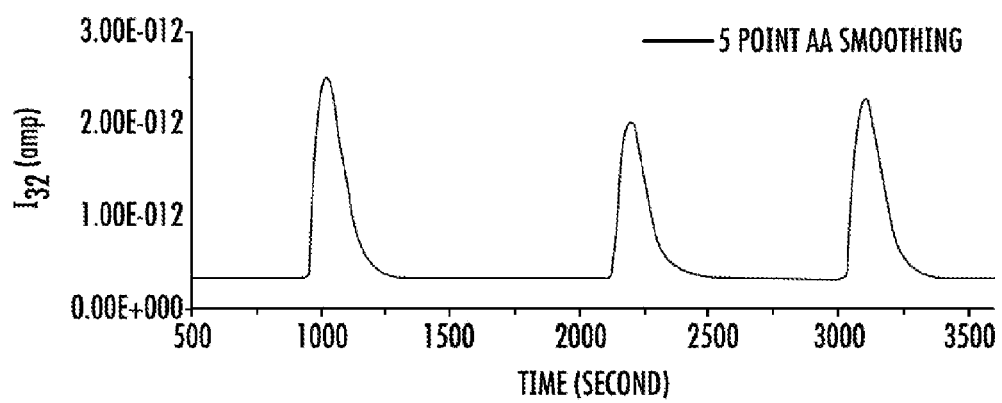
FIG. 10 illustrates (a) A gas pulse test; (b) estimation of $t_d$; (c) estimation of $t_p$ in accordance with certain embodiments of the present disclosure.
Figure 10B:
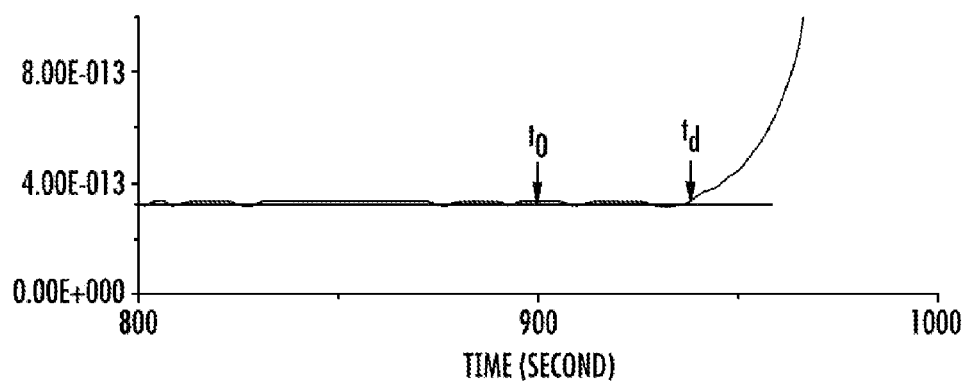
Figure 10C:
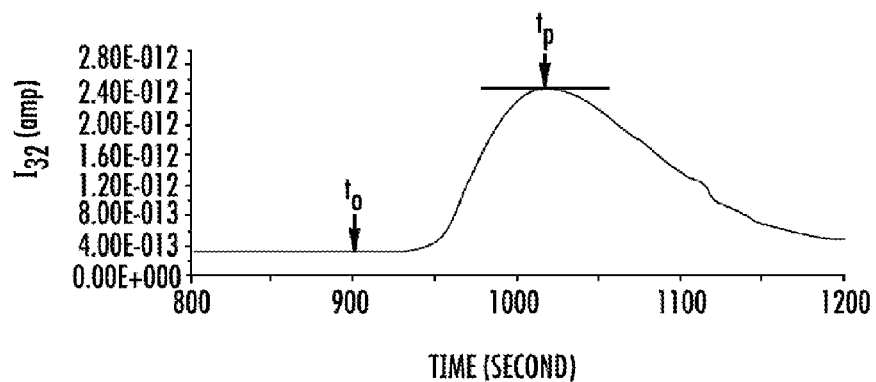
Figure 11A:
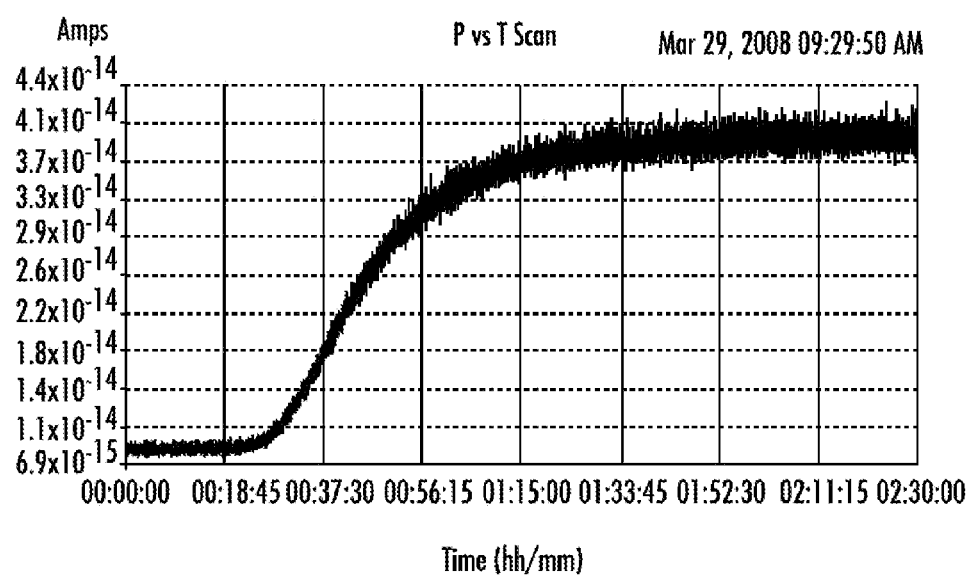
FIG. 11 illustrates (a) A real-time experimental data curve recorded during the $CO_2$ permeation through a 1-mil thick Mylar® film, on which the data given in the second row of TABLE II is based; (b) smoothed experimental data using 5-point averaging; (c) time-lag analysis applied to the smoothed experimental data.
Figure 11B:
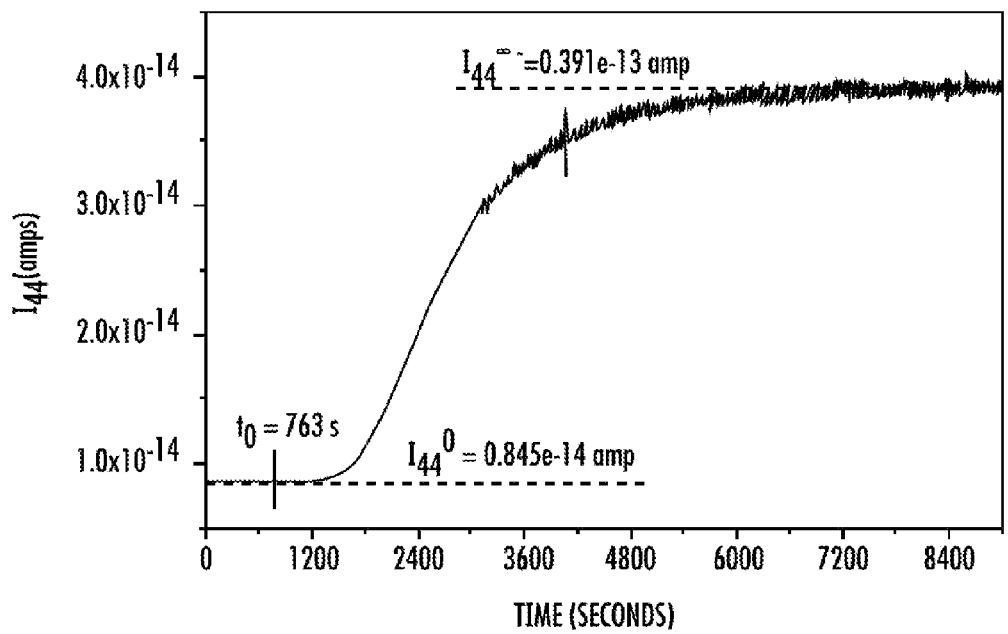
Figure 11C:
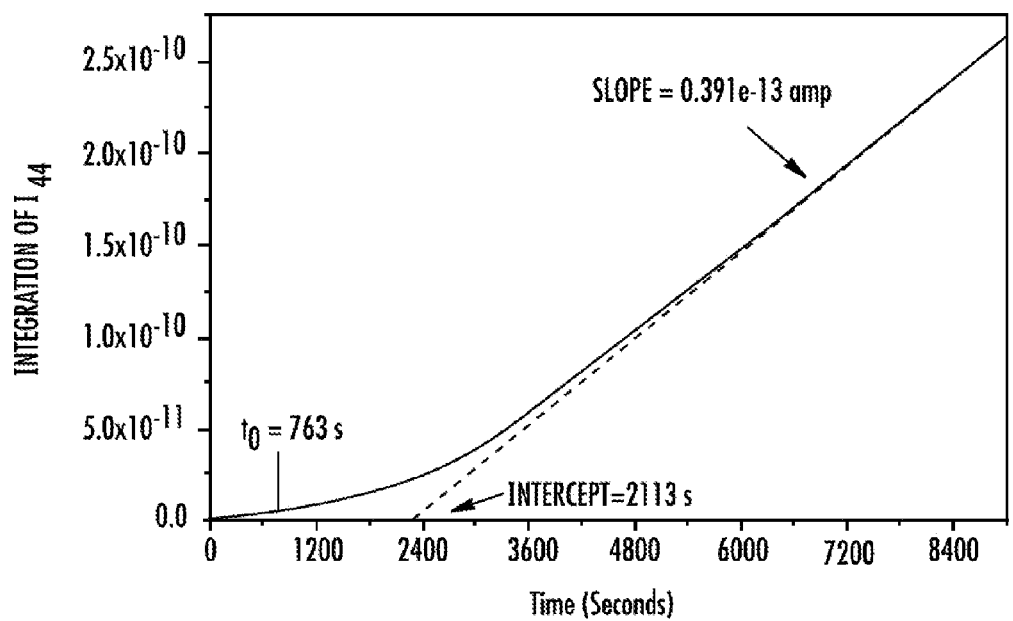

The total system time delay includes the traveling time in the tubing connections, the time for the gas to flush the permeation cell and to reach the sorption equilibrium on the test film surface, and the dead time in the variable leak valve. The process to reach the sorption equilibrium at the film surface happens simultaneously when the gas is flushing the supply volume. It is difficult to determine the sorption time constant. If we assume the sorption happens quickly enough, the sorption time constant is included in the time to flush the cell. The total system time delay may be approximately determined by a gas pulse test, whose experimental setup is schematically drawn in FIG. 9. In a gas pulse test, the permeation cell is clamped without the test film, and only one inlet and one outlet of the cell are open to the gas. This setup allows a gas stream to pass directly through the cell. The cell is flushed with the carrier gas first, with the principal mass peak of the test gas continuously monitored by the QMS. Denote the time when the valve is switched to the testing gas as $t_0$, and the time when the signal starts to deviate from the base line as $t_d$, and the time when the signal arrives at its peak level as $t_p$. The time constant is taken as the interval between $t_0$ and $t_d$. Obviously, the time constant depends on the gas flow rates when other conditions remain unchanged. An example of such a gas pulse test is shown in FIG. 10, which uses oxygen as the test gas. The time constants were determined at three different flow rates, each with three measurements. The results are summarized in Table 1. The results indicate that the time constant is inversely liner with the flow rate. Hence the system time delay is mainly comprised of the delay spent on the travel in the tubing and other system components (mass flow controller and permeation cell) and the dead time in the variable leak valve is negligible.

Adjustment of Quadrupole Mass Spectrometer

For quantitative analysis and comparison purposes, all operations with quadrupole mass spectrometer must be performed under the same hardware and software settings. The hardware settings are factory-set and stored in the non-volatile memory in the device. The RGA_3.0 software provides options to tune mass peak position and sensitivity and electronic multiplier gain. The changes to the hardware settings are made automatically by the software.

The choice of scan speed affects the signal quality. The faster the scan speed, the higher the noise level. It is important that the calibrations and the measurements are performed at the same operational settings.

Deterioration of the electron multiplier is inevitable. The CEM gain may be restored by raising the bias voltage through the established tuning procedure. In case the CEM degrades to such an extent that it can no longer produce desirable gain under the applied voltage, its efficiency may be restored to almost new conditions with a bake in oxygen.

General Test Procedures

It is recommended to bake the vacuum chamber at $\leqq 200°$ C. prior to measurement.

The devices including the QMS and the mass flow controllers should be allowed to warm up at least for one hour or longer (with filament on) to ensure stability before any measurement is made. The vacuum chamber pressure is typically around $10^{-6}$ torr and the carrier gas flow rate is typically around 5 cc/min.

The sensitivity factors for the gases involved in the experiment are calibrated off-line using the second calibration method as described above.

The carrier gas should be inert and its mass spectrum should not interfere with that of the test gas.

The experimental setup as illustrated in FIG. 1 is used. The permeation cell is sealed with O-ring and sealing grease. The size of the test specimen is about 2.5" in diameter. Its thickness depends on the expected permeation rate and its strength. Films with thickness ranging from 1.5 microns to 35 microns have been tested.

Before taking any measurement, the flow lines are purged with the designated gases. The outlet pressures of the test gas cylinder and the carrier gas cylinder are set equal. The test film is conditioned by flushing an inert carrier gas on both sides for some period.

The RGA_3.0 window is set to the P vs T scan mode. The scan speed, detector type and the mass locations to be monitored are set in the 'scan parameter' menu.

After warm-up, start the P vs T scan and start counting time. The background signal is collected first to establish the baseline, $I_0$. Switch the flush gas stream to the test gas stream when the permeation test begins; the time is registered as $t_0$. In general, the test should be allowed to reach steady state to establish $I_\infty$. The duration of the test should be at least 3 times longer than the estimated time lag. Switch the test gas to the flush gas when the permeation test ends; the time is registered as $t_f$. The permeability and diffusion constants are determined according to the methods in 3.

The sensitivity factors may be recalibrated to ensure there is no degradation of the detector.

The test method may be conducted with test and carrier gases at controlled temperature ($\leqq 75°$ C.) and any relative humidity.

Experimental Example

The film materials used in the permeation tests were 1-mil thick Mylar® PET provided by Eastman Chemical Company. The test gas was $CO_2$. The permeability of the film for $CO_2$ at room temperature was measured to be 1.18 $(cm^3 \cdot cm)/(cm^2 \cdot s \cdot Pa)$ using a Mocon instrument located at an Eastman facility. The permeability value is reported in the literature to be 1.15 $(cm^3 \cdot cm)/(cm^2 \cdot s \cdot Pa)$ at 30° C. The diffusivity value as reported is $5.4 \times 10^{-10}$ $cm^2/sec$.

The Mylar® PET was tested at close to room temperature (about 21° C. - about 23° C.) using the current method. The results are summarized in Table 2. These tests were carried out over a period of time and the actual settings were different from each other. Modest degradation of the electron multiplier was observed between Tests 2 and 3. However, the results are in good agreement with each other. The estimated permeability values are in excellent agreement with the value obtained with Mocon instrument. The difference is considered within measurement error (5-10%). Notably, the diffusivity values also agree well with the literature value as seen in Table II.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

What is claimed is:

1. A system for determining the rate of gas permeation through a film comprising:

a continuous flow permeation cell, a mass spectrometer, a computer configured to receive data from the mass spectrometer, a test gas source, and a carrier gas source, the continuous flow permeation cell comprising a supply chamber in communication with the test gas source and a receiving chamber in communication with the carrier gas source and the mass spectrometer, wherein the supply chamber is configured to be separated from the receiving chamber by a test film such that when a test gas stream is fed to the supply chamber from the test gas source and a carrier gas stream is fed to the receiving chamber from the carrier gas source, at least a portion of the test gas stream permeates from the supply chamber through the test film to the receiving chamber and mixes with the carrier gas stream and the mixture flows to a gas inlet channel of a variable leak valve such that the mixture discharges at an end of the gas inlet channel immediately adjacent to the variable leak valve to reduce dead volume and passes through the variable leak valve to the mass spectrometer, the variable leak valve configured to permit only a small volume of the mixture to be sampled by the mass spectrometer and limit time delay associated therewith, data received from the mass spectrometer being utilized by the computer to determine the rate of permeation of the test gas stream through the film.

2. The system of claim 1, wherein the mass spectrometer is a quadrupole mass spectrometer.

3. The system of claim 1, wherein the continuous flow permeation cell further comprises a temperature control.

4. The system of claim 1, wherein the test gas stream comprises a single gas.

5. The system of claim 1, wherein the test gas stream comprises a mixture of more than one gas, the mass spectrometer being capable of measuring the rate of permeation of each individual test gas in the mixture.

6. The system of claim 1, wherein the computer includes software, the software capable of permitting a user to adjust the sensitivity of the mass spectrometer.

7. The system of claim 1, wherein the mass spectrometer further comprises a high vacuum chamber.

8. The system of claim 1, wherein the carrier gas has a flow rate, the carrier gas flow rate being utilized to determine the rate of permeation of the test gas stream through the film.

9. The system of claim 1, wherein the carrier gas is an inert gas.

10. A method for determining the rate of gas permeation through a film comprising:

feeding a test gas stream through a test film in a system, the system comprising a continuous flow permeation cell, a mass spectrometer, a computer configured to receive data from the mass spectrometer, a test gas source, and a carrier gas source, the continuous flow permeation cell comprising a supply chamber in communication with the test gas source and a receiving chamber in communication with the carrier gas source and the mass spectrometer, wherein the supply chamber is configured to be separated from the receiving chamber by a test film such that when the test gas stream is fed to the supply chamber from the test gas source, a carrier gas stream is fed to the receiving chamber from the carrier gas source and at least a portion of the test gas stream permeates from the supply chamber through the test film to the receiving chamber and mixes with the carrier gas stream and the mixture flows to a gas inlet channel of a variable leak valve such that the mixture discharges at an end of the gas inlet channel immediately adjacent to the variable leak valve to reduce dead volume and passes through the variable leak valve to the mass spectrometer, the variable leak valve configured to permit only a small volume of the mixture to be sampled by the mass spectrometer and limit time delay associated therewith; and the computer utilizing data received from the mass spectrometer to determine the rate of permeation of the test gas stream through the film.

11. The method of claim 10, wherein the mass spectrometer is a quadrupole mass spectrometer.

12. The method of claim 10, wherein the continuous flow permeation cell further comprises a temperature control.

13. The method of claim 10, wherein the test gas stream comprises a single gas.

14. The method of claim 10, wherein the test gas stream comprises a mixture of more than one gas, the mass spectrometer being capable of measuring the rate of permeation of each individual test gas in the mixture.

15. The method of claim 10, wherein the computer includes software, the software capable of permitting a user to adjust the sensitivity of the mass spectrometer.

16. The method of claim 10, wherein the mass spectrometer further comprises a high vacuum chamber.

17. The method of claim 10, wherein the carrier gas has a flow rate, the carrier gas flow rate being utilized to determine the rate of permeation of the test gas stream through the film.

18. The method of claim 10, wherein the carrier gas is an inert gas.

* * * * *